United States Patent [19]

Mitsuhashi et al.

[11] Patent Number: 4,659,569
[45] Date of Patent: Apr. 21, 1987

[54] PROCESS FOR THE PRODUCTION OF VIRUS VACCINE

[75] Inventors: Masakazu Mitsuhashi; Shunsaku Koyama, both of Okayama, Japan

[73] Assignee: Kabushiki Kaisha Hayashibara Seibutsu Kagaku Kenkyujo, Okayama, Japan

[21] Appl. No.: 336,943

[22] Filed: Jan. 4, 1982

[30] Foreign Application Priority Data

Feb. 9, 1981 [JP] Japan .................. 56-17643

[51] Int. Cl.$^4$ .................. A61K 39/12; A61K 39/145; A61K 39/165; A61K 39/17
[52] U.S. Cl. ...................... 424/89; 435/236; 435/238; 424/86; 530/387; 530/404; 530/406; 530/413; 530/806; 530/825
[58] Field of Search .................. 424/89, 85, 88, 86; 435/236, 238; 530/387, 404, 406, 413, 806, 825

[56] References Cited

U.S. PATENT DOCUMENTS 4,003,792 1/1977 Mill et al. .................. 424/89
4,372,883 2/1983 Matuhashi et al. .............. 424/92 X

FOREIGN PATENT DOCUMENTS 2499414 8/1982 France .
2499412 8/1982 France .
35325 1/1975 Japan .
2061955A 5/1981 United Kingdom .
2096146A 10/1982 United Kingdom .
2095552A 10/1982 United Kingdom .

OTHER PUBLICATIONS

Veith et al., "Enzyme Engineering", *Chemtech*, Jan. 1974, pp. 47-55.
*The American Type Culture Collection, Catalogue of Strains II,* Second Edition, 1979, pp. 148, 168, and 169.
Fielder et al., J. Immun., vol. 105, No. 1, pp. 265-267 (1979).
Schneerson et al., J. Exp. Med., vol. 152, pp. 361-376 (1980).

*Primary Examiner*—Shep K. Rose
*Attorney, Agent, or Firm*—Browdy and Neimark

[57] ABSTRACT

The present invention relates to a process for the production of virus vaccine, comprising covalently attaching virus to saccharide to form a virus-saccharide conjugate, and harvesting the resultant conjugate. The virus vaccine, prepared according to the present invention, exhibits a higher producibility of immunoglobulin G and immunoglobulin M antibodies, while it induces less or substantially no production of immunoglobulin E antibody, in comparison with conventional-type inactivated virus vaccine; thus, the present vaccine is favorably usable for the prevention and treatment of viral diseases.

8 Claims, No Drawings

PROCESS FOR THE PRODUCTION OF VIRUS VACCINE

DETAILED DESCRIPTION OF THE INVENTION

The present invention relates to a process for the production of virus vaccine, characterized by covalently attaching virus to saccharide to form a virus-saccharide conjugate, and harvesting the resultant conjugate.

Conventionally, virus vaccines have been prepared by inactivating and detoxifying virus with formalin or β-propiolactone without decreasing its immunogenicity, or alternatively isolating a certain virus strain with less toxicity. Such vaccines have been used for prophylactic, therapeutic and/or diagnostic trials of viral diseases.

Conventional-type virus vaccine, however, disadvantageously produces immunoglobulin E antibody which causes allergy diseases and/or anaphylactic-shock, but produces other antibodies, e.g., immunoglobulin G and immunoglobulin M antibodies, which are effective in prevention of viral infections, to a diminished extent in comparison with intact virus.

The present inventors investigated processes for the production of virus vaccine wherein the producibility of immunoglobulin E antibody, which causes allergy diseases and/or anaphylactic-shock, is remarkably suppressed without decreasing the producibility of immunoglobulin G and immunoglobulin M antibodies which are effective in the prevention of viral diseases.

These efforts have resulted in the finding that the present objectives can be attained with a virus-saccharide conjugate which can be obtained by covalently attaching virus to saccharide.

The viruses feasible and applicable in the present invention are those which cause viral disease in animals and/or humans, and which stimulate the production of immunoglobulin antibodies therein. For example, vaccinia virus, poliovirus, influenza virus, Japanese encephalitis virus, yellow fever virus, measles virus, rubella virus, mumps virus, hepatitis B virus, adeno virus, Epstein-Barr virus, distemper virus, rabies virus, Sendai virus and Newcastle disease virus are all feasible and applicable in the present invention.

The virus can be subjected intact, or, if necessary, after treatment with acid, alkali, heating, UV-irradiation and/or organic solvent, to conjugation reaction with an activated saccharide.

The saccharides usable in the invention are polysaccharides, e.g., starch, amylose, dextran, poly-sucrose or Ficoll (Pharmacia Fine Chemicals AB, Uppsara, Sweden), pullulan, elsinan, curdlan, gum arabic, gum tragacanth, guar gum, xanthan gum, carrageenan, pectin, cellulose, glucomannan and chitosan; and their derivatives and partial hydrolysates, average molecular weights of which are generally in the range of 1,000–10,000,000, preferably, in the range of 10,000–1,000,000.

Especially, pullulan, elsinan and their partial hydrolysates are suitable for the present objectives because the covalent attachment between the virus and any of them remarkably enhances the inherent producibility of immunoglobulin G and immunoglobulin M antibodies, and substantially diminishes the immunoglobulin E antibody producibility, as well as sufficiently inactivating and detoxifying the virus.

As to the method for covalent attachment of virus to saccharide, any method can be employed in the present invention so far as the virus is covalently attached to the saccharide thereby, for example, diazo-coupling, peptide, alkylation, cross-linking.

The diazo-coupling method is a method wherein the virus is subjected to a conjugation reaction with a saccharide bearing aromatic amino group(s), e.g., p-aminobenzyl, p-aminobenzoyl, m-aminobenzyl, m-aminobenzoyl, m-aminoanisoyl, m-aminobenzyl oxymethyl, 3-(p-aminophenoxy)-2-hydroxy propionyl or 3-(p-amino-m-methylanilino)-5-chlorotriazinyl group, which are introducible by conventional methods.

In the peptide method, the virus is subjected to a conjugation reaction with a carbonate derivative, e.g., acid azide, acid chloride, carbodiimide or isocyanate derivative, obtained from carboxyl saccharide, or with an imino ester derivative, e.g., BrCN-activated saccharide.

The alkylation method involves a conjugation reaction of the virus with a saccharide derivative which bears a halogenoalkyl group, e.g., a chloroacetyl, bromoacetyl, iodoacetyl or chlorotriazinyl group.

The cross-linking method involves a cross-linking reaction between the virus protein and saccharide in the presence of a polyfunctional reagent, e.g., glutaraldehyde, glyoxal, succindialdehyde, hexamethylene diisocyanate, toluene 2,4-diisocyanate, bis-azobenzidine or N,N'-ethylene-bis-maleimide.

The weight ratio of virus versus saccharide in the conjugation reaction should be generally in the range of 1:1,000–1,000:1, preferably in the range of 1:100–100:1.

In the course of the conjugation reaction, more than one variety of both virus and saccharide may be used. Thus, conjugation of one variety of virus with two or more varieties of saccharides, or conjugation of one variety of saccharide with two or more varieties of viruses, is possible to obtain a mixed vaccine preparation.

As to the reaction conditions for conjugation, any conditions can be applied so far as the conjugation does inactivate and detoxify the virus, and substantially diminishes its producibility of immunoglobulin E antibody, which causes allergy diseases and/or anaphylactic-shock, without decreasing the producibility of immunoglobulin G and immunoglobulin M antibodies which are effective in the prevention of viral diseases. Generally, the conjugation reaction is effected at a reaction temperature of about 0°–100° C. and a reaction pH of about 3–12 for about 0.1–50 hours.

The virus vaccine thus obtained can be generally subjected to separation and/or purification steps using conventional procedures, e.g., filtration, washing, centrifugation, salting-out, dialysis, adsorption and desorption with absorbent, gel filtration, ion exchange chromatography, affinity chromatography and/or electrophoresis, and concentrated into a virus vaccine in liquid or paste form which may be prepared into powder by subsequent drying.

The virus vaccine can be favorably used alone or, if necessary, in combination with another agent, e.g., antiseptic agent or adjuvant, as a prophylactic, therapeutic or diagnostic agent, desensitizer or interferon inducer in the prevention and treatment of human or animal viral diseases.

Additionally, according to the present invention, the detoxification of the virus can be performed within a brief time, i.e., generally within 1-2 days, and the resultant virus vaccine is very stable over a long period of time without fear of restoration of toxicity, while conventional processes using formalin require much longer times, i.e., generally 20-90 days, for detoxification of the virus, and the resultant conventional-type virus vaccine tends to eventually have its toxicity restored. Thus, an adequate storage and production of virus vaccine to overcome the prevalence or outbreak of viral diseases can be easily achieved.

Furthermore, the process does not necessarily require a highly-purified virus preparation because it avoids contamination of other proteins, e.g., those from the culture medium which cause fatal allergies and/or anaphylactic-shock. According to the present invention, a crude virus preparation can be directly inactivated and detoxified without complicated purification steps, providing a large amount of virus vaccine at a low-cost.

In addition to the above described features, it has been confirmed that a virus vaccine obtained with a crude virus preparation exhibits a comparable or even higher immunological activity than that obtained with a highly-purified preparation.

Several embodiments of the present invention are disclosed hereinafter.

EXAMPLE 1

Japanese encephalitis virus vaccine

1. Preparation of Japanese encephalitis virus

Japanese encephalitis virus Nakayama strain was inoculated in 4-week-old mice, and the animals were fed for about 80 hours until they were completely paralysed. After removing their brains by incision, the brains were suspended in 4 volumes of physiological saline solution, containing 1/15M phosphate buffer (pH 8.0), and homogenized therein. The resultant was then centrifuged at $3,000 \times g$ for 20 minutes, and the supernatant was added with an aqueous protamine sulfate solution to give a concentration of 2 mg per ml. The admixture was then stirred for two hours, and centrifuged to obtain a supernatant containing Japanese encephalitis virus.

The supernatant contained about 0.8 w/v % Japanese encephalitis virus.

2. Conjugation of Japanese encephalitis virus to pullulan

To a pullulan solution, prepared by dissolving 5.2 g pullulan having an average molecular weight of 100,000 in 110 ml dimethyl formamide with heating and cooling to ambient temperature, was added 10 ml pyridine, and the mixture was added with 1.0 g p-nitro benzoyl chloride with stirring. Thereafter, the mixture was allowed to standing at ambient temperature for 17 hours. To the resultant was added two volumes of n-propyl alcohol, and the precipitate was collected. The precipitate was dissolved again in fresh dimethyl formamide. The above precipitation-dissolution operation was repeated three times, and the finally-obtained precipitate was dissolved in 5 w/v % aqueous sodium dithionite solution. After incubating the mixture at 80° C. for 30 minutes, the resultant was decolorized with activated carbon, followed by adding thereto with two volumes of n-propyl alcohol to effect precipitation. The obtained precipitate was dissolved in water, and dialyzed against running tap water overnight.

After cooling the dialyzed solution to a temperature below 2° C., to the solution was added hydrochloric acid to give a concentration of about 0.1N, and the mixture was further added with sodium nitrite to give a concentration of about 1 w/v %, under stirring conditions. The admixture was then subjected to diazotization reaction at this temperature for 30 minutes. After completion of the reaction, the reaction mixture was dialyzed against distilled water for two hours at a temperature below 2° C. to obtain an activated pullulan solution.

To the solution was added 100 ml of the Japanese encephalitis virus solution, obtained in EXAMPLE 1—(1) and preinactivated by 3-hour heating at 60° C., and the mixture was adjusted to pH 8.5 with sodium carbonate solution. Thereafter, the mixture was subjected to diazo-coupling reaction at a temperature below 4° C. for two hours with stirring. To the reaction mixture was added three volumes of acetone, and the resultant precipitate was collected. After dissolving the precipitate in 0.01M phosphate buffer (pH 7.0), the solution was centrifuged to remove insoluble substance. The supernatant was fractionated with gel filtration procedure to obtain a fraction containing the Japanese encephalitis virus-pullulan conjugate which was then carefully filtered, concentrated, and lyophilized, obtaining a powder Japanese encephalitis virus vaccine in the yield of about 60% against the starting virus material.

Control vaccine was prepared as follows: To 50 ml of the virus solution, obtained in EXAMPLE 1—(1), was added 0.05 v/v % Japanese Pharmacopoeial formalin solution, and the mixture was allowed to a stand at 4° C. for 60 days to inactivate the virus. The resultant was centrifuged at $3,000 \times g$ for 20 minutes, and the supernatant was subjected to careful filtration, concentration and lyophilization in the given order, obtaining a control Japanese encephalitis virus vaccine in the yield of about 50% against the starting virus material.

3. Administration of Japanese encephalitis virus vaccine into mouse

Intravenous injection of the virus solution, obtained in EXAMPLE 1—(1), into (DDD×BALB/C) $F_1$ mice in an inoculum of $5 \times 10^{-8}$ g per animal resulted in their incidence of Japanese encephalitis to death.

On the contrary, intravenous injection of either the present virus vaccine or control vaccine in mice of the same strain in an inoculum of up to $10^{-3}$ g in terms of intact virus did not result in their death, confirming that both vaccines were sufficiently inactivated and detoxified.

Separately, after injecting intravenously into mice of the same strain with either the present virus vaccine or the control vaccine in an inoculum of $5 \times 10^{-5}$ g in terms of intact virus, the animals were further injected with respective vaccine 7 days after the first injection. The animals were bled 10 days after the first injection, and the antibody production in their sera was determined. The production of immunoglobulin G and immunoglobulin M antibodies was assayed by the Passive Haemagglutination (PHA) reaction, and the immunoglobulin E antibody production was assayed by the Passive Cutaneous Anaphylaxis (PCA) reaction.

The above experiments confirmed that an about 16-fold higher production of immunoglobulin G and immunoglobulin M antibodies was obtained with the present vaccine, and that no detectable immunoglobulin E antibody was formed simultaneously. On the other hand, a significant amount of immunoglobulin E antibody was formed with the control vaccine, which corresponded to about half of the immunoglobulin G and immunoglobulin M antibody production obtained therewith.

A test, wherein either the present vaccine or the control vaccine was incubated at 40° C. in 0.1M phosphate buffer (pH 7.0) containing 0.01 v/v % Japanese Pharmacopoeial formalin as an antiseptic agent, and wherein the amount of the formed immunoglobulin G and immunoglobulin M antibodies was determined by PHA reaction after administering the incubated vaccine in mouse, confirmed that the immunological half life of the present vaccine was about 8-times longer than that of the control vaccine.

Accordingly, the present vaccine is favorably usable as a Japanese encephalitis virus vaccine without fear of allergy diseases and/or anaphylactic-shock because of its satisfactory stability.

EXAMPLE 2

Japanese encephalitis virus vaccine

To an aqueous elsinan solution, prepared by dissolving 8 g elsinan with an average molecular weight of about 700,000 in 200 ml hot water and cooling to ambient temperature, was added 10% cyanuric chloride in 40 ml dimethyl formamide, and the mixture was adjusted to pH 7.0, followed by subjecting the mixture to activation reaction for two hours under ambient conditions while keeping the pH level with 1N sodium carbonate solution. The reaction mixture was then dialyzed against water at 4° C. and this pH level overnight to obtain an activated elsinan solution.

To the solution was added 45 ml of the Japanese encephalitis virus solution, obtained similarly as in EXAMPLE 1—(1) and preinactivated by UV-irradiation, and the mixture was adjusted to pH 9.0, followed by standing for two hours under ambient and stirring conditions to effect conjugation reaction. Thereafter, the resultant was purified similarly as in EXAMPLE 1—(2), obtaining a Japanese encephalitis virus vaccine powder in the yield of about 60% against the starting virus material.

Intravenous injection of the vaccine thus obtained was carried out similarly as in EXAMPLE 1—(3), and confirmed that the vaccine was sufficiently inactivated and detoxified.

Also, the production of immunoglobulin G and immunoglobulin M antibodies was about 10-fold higher than that with the control vaccine, prepared in EXAMPLE 1—(2), and no detectable immunoglobulin E antibody was formed simultaneously.

The immunological half life of the present vaccine was about 4-times longer than that of the control vaccine.

Thus, the present vaccine is favorably usable as a Japanese encephalitis virus vaccine.

EXAMPLE 3

Japanese encephalitis virus vaccine

A Japanese encephalitis virus vaccine was prepared similarly as in EXAMPLE 1—(2), except that the pullulan was substituted with a dextran having an average molecular weight of 70,000. The yield was about 40% against the starting virus material.

Administration test on the vaccine was carried out similarly as in EXAMPLE 1—(3), and confirmed that the vaccine was sufficiently inactivated and detoxified.

The production of immunoglobulin G and immunoglobulin M antibodies with the present vaccine was about 16-fold higher than that with the control vaccine, prepared in EXAMPLE 1—(2), while the production of immunoglobulin E antibody was only about 1/64 of that with the control vaccine.

Also, the immunological half life of the present vaccine was about 2-times longer than that of the control vaccine.

Thus, the present vaccine is favorably usable as a Japanese encephalitis virus vaccine.

EXAMPLE 4

Influenza virus vaccine

1. Preparation of influenza virus

Influenza virus A/Tokyo/6/73 (H3N2) strain was inoculated in 10-day-old embryonated eggs, and the eggs were incubated at 36° C. for three days, followed by collection of their allantoic fluid. The allantoic fluid was centrifuged at 2,000×g for 20 minutes, and the supernatant was filtered with a membrane filter having a nominal pore size of $0.8\mu$, obtaining a solution containing influenza virus.

2. Conjugation of influenza virus to pullulan partial hydrolysate

An aqueous pullulan solution, prepared by dissolving 5 g pullulan partial hydrolysate with an average molecular weight of about 10,000 in 400 ml water, and the mixture was adjusted to pH 10.7 with 1N sodium hydroxide solution. To the solution was added gradually 3 g BrCN while keeping the pH level and stirring, and the admixture was then allowed to stand under these conditions for one hour to effect activation reaction. After adjusting the reaction mixture to pH 5.0 with 1N hydrochloric acid, the mixture was dialyzed against chilled water at this pH level to obtain an activated pullulan solution.

After adjusting the solution to pH 8.0 with 0.05M carbonate buffer, to the solution was added 200 ml of the influenza virus solution, obtained in EXAMPLE 4—(1), and the mixture was subjected to conjugation reaction for 24 hours under ambient conditions. The reaction mixture was purified, concentrated, and lyophilized similarly as in EXAMPLE 1—(2), obtaining a powder influenza virus vaccine in the yield of about 70% against the starting virus material.

Control vaccine was prepared as follows: To the influenza virus solution, obtained in EXAMPLE 4—(1), was added two volumes of ether, and the mixture was incubated at 4° C. for two days. The resultant was filtered, and the filtrate was lyophilized to obtain a control powder vaccine preparation in the yield of about 60% against the starting virus material.

3. Administration of influenza virus vaccine into mouse

Intravenous injection of the vaccine thus obtained was carried out similarly as in EXAMPLE 1—(3) into mice of the same strain, and confirmed that both vaccines were sufficiently inactivated and detoxified.

The production of immunoglobulin G and immunoglobulin M antibodies with the present vaccine was about 8-fold higher than that with the control vaccine, and no detectable immunoglobulin E antibody was formed simultaneously.

On the contrary, a significant amount of immunoglobulin E antibody was formed with the control vaccine, which corresponded to about half of the immunoglobulin G and immunoglobulin M antibody production obtained therewith.

Accordingly, the present vaccine is favorably usable as an influenza virus vaccine.

EXAMPLE 5

Sendai virus vaccine

1. Preparation of Sendai virus

Sendai virus was inoculated in 10-day-old embryonated eggs which were then incubated similarly as in EXAMPLE 4—(1). The allantoic fluid of the eggs were collected, and purified similarly as in the same EXAMPLE, obtaining a supernatant containing Sendai virus.

2. Conjugation of Sendai virus to pullulan

To an aqueous pullulan solution, prepared by dissolving 10 g pullulan with an average molecular weight of 70,000 in 200 ml water with heating and cooling to ambient temperature, was added 5 g hexamethylene diamine, and the mixture was adjusted to pH 11.0 with 1N sodium hydroxide solution. The mixture was then cooled to a temperature below 20° C. with ice bath, and added gradually with 5 g BrCN while stirring and keeping the pH level, followed by 30-minute standing under these conditions. The reaction mixture was dialyzed against distilled water at 4° C. for one hour to obtain an activated pullulan solution.

To the solution was added 25 w/v % glutaraldehyde in 2 ml water, 60 ml of the Sendai virus solution, obtained in EXAMPLE 5—(1), and 10 ml of 1M acetate buffer (pH 5.0), and the mixture was subjected to conjugation reaction at 4° C. for 24 hours under stirring conditions. The conjugation reaction was suspended by adding thereto glycine to give a concentration of 1M and allowing the admixture to stand at ambient temperature for 24 hours. The resultant was centrifuged, and the supernatant was fractionated with gel filtration technique to obtain a fraction containing a Sendai virus-pullulan conjugate. The fraction was then concentrated, carefully filtered, and finally added with Japanese Pharmacopoeial formalin as an antiseptic agent to give a concentration of 0.01 v/v %, obtaining a liquid Sendai virus vaccine in the yield of about 50% against the starting virus material.

Control vaccine was prepared as follows: To the Sendai virus solution, obtained in EXAMPLE 5—(1), was added Japanese Pharmacopoeial formalin to give a concentration of 0.05 v/v %, and the mixture was incubated at 4° C. for 60 hours to inactivate the virus. The resultant was then centrifuged at 3,000×g for 20 minutes, and the supernatant was carefully filtered, obtaining a control liquid vaccine preparation in the yield of about 40% against the starting virus material.

3. Administration of Sendai virus vaccine into mouse

Administration test on the vaccines thus obtained was carried out similarly as in EXAMPLE 1—(3), and confirmed that both vaccines were sufficiently inactivated and detoxified.

The production of immunoglobulin G and immunoglobulin M antibodies with the present vaccine was about 10-fold higher than that with the control vaccine, and no detectable immunoglobulin E antibody was formed simultaneously.

On the contrary, a significant amount of immunoglobulin E antibody was formed with the control vaccine, which corresponded to about half of the immunoglobulin G and immunoglobulin M antibody production obtained therewith.

Accordingly, the present vaccine is favorably usable as a Sendai virus vaccine.

EXAMPLE 6

Measles virus vaccine

1. Preparation of measles virus

Vero cells, derived from green monkey kidney (GMK), were infected with measles virus Edmonston strain in Eagle's medium, supplemented with 5 v/v % calf serum, and cultivated therein at 37° C. for seven days. After completion of the cultivation, the culture was centrifuged at 3,000×g for 20 minutes, and the supernatant was further centrifuged at 110,000×g for 30 minutes. The sediment was suspended in physiological saline solution to double the total volume, obtaining a solution containing measles virus.

2. Conjugation of measles virus to carboxymethyl cellulose

To 200 ml of an aqueous 1 w/v % carboxymethyl cellulose solution with an average molecular weight of 20,000, was added 2 g 1-ethyl-3-(3-dimethyl amino)propyl carbodiimide, and the mixture was adjusted to pH 4.0 with hydrochloric acid, followed by standing with stirring at this pH level and ambient temperature for two hours to effect activation reaction. The reaction mixture was then dialyzed against distilled water to obtain an activated carboxymethyl cellulose solution.

To the solution was added 90 ml of the measles virus solution, obtained in EXAMPLE 6—(1), and the mixture was subjected to conjugation reaction at ambient temperature overnight while stirring and keeping at pH 4.5. Thereafter, the reaction mixture was centrifuged, and the supernatant was fractionated by gel filtration technique to obtain a fraction containing a measles virus-carboxymethyl cellulose conjugate. The fraction was carefully filtered, and the filtrate was added with thimerosal as an antiseptic agent to give a concentration of 0.01 w/v %, obtaining a liquid measles virus vaccine in the yield of about 50% against the starting virus material.

Control vaccine was prepared as follows: The measles virus solution, obtained in EXAMPLE 6—(1), was treated similarly as in the control vaccine of EXAMPLE 1—(3), obtaining a control vaccine in the yield of about 40% against the starting virus material.

3. Administration of measles virus vaccine into mouse

Intravenous injection test on the vaccines thus obtained was carried out similarly as in EXAMPLE 1—(3), and confirmed that both vaccines were sufficiently inactivated and detoxified.

The production of immunoglobulin G and immunoglobulin M antibodies with the present vaccine was about 4-fold higher than that with the control vaccine, while no detectable immunoglobulin E antibody was formed simultaneously.

On the contrary, a significant amount of immunoglobulin E antibody was formed with the control vaccine, which corresponded to about ¼ of the immunoglobulin G and immunoglobulin M antibody production obtained therewith.

Accordingly, the present vaccine is favorably usable as a measles virus vaccine.

EXAMPLE 7

Newcastle disease virus vaccine

Newcastle disease virus with less toxicity (Ishii strain) was inoculated in 8-day-old embryonated eggs which were then incubated similarly as in EXAMPLE 4—(1). After the incubation, the allantoic fluid was collected therefrom, and treated similarly as in EXAMPLE 6—(1), obtaining a solution containing Newcastle disease virus.

To 100 ml of the virus solution was added an activated pullulan solution, prepared similarly as in EXAMPLE 1—(2), and the mixture was subjected to conjugation reaction at pH 8.0 under ambient conditions for 24 hours. The resultant conjugate was separated, purified, and lyophilized similarly as in EXAMPLE 1—(2), obtaining a powder Newcastle disease virus vaccine in the yield of about 50% against the starting virus material.

Since the present vaccine remarkably prevents viral infection without causing allergy diseases and/or anaphylactic-shock, it is favorably usable as a Newcastle disease virus vaccine.

What is claimed is:

1. A process for producing virus vaccine having a substantially diminished immunoglobulin E antibody producibility and remarkably enhanced producibility of immunoglobulin G and immunoglobulin M antibodies, said process comprising the steps of:

providing a water-soluble polysaccharide selected from the group consisting of pullulan, elsinan, hydrolysates thereof, and mixtures thereof, said polysaccharide having a molecular weight from 1,000 to 100,000,000, and bearing a functional group capable of covalently linking with a pathogenic virus, said functional group being a member selected from the group consisting of carbodimide, imidocarbonate, halogenoalkyl, aldehyde and isocyanate groups, and aromatic amino groups in the form of diazonium salts;

forming a water-soluble conjugate of a pathogenic virus and said polysaccharide by allowing one part by weight of the virus to react with 0.01 to 100 parts by weight of the polysaccharide at a pH in the range of 3 to 12 and a temperature in the range of 0° to 100° C. for 0.1 to 50 hours to thereby detoxify said virus; and recovering said water-soluble conjugate for use as a virus vaccine having a substantially diminished immunoglobulin E antibody producibility and remarkably enhanced producibility of immunoglobulin G and immunoglobulin M antibodies.

2. The process of claim 1, wherein said pathogenic virus is selected from the group consisting of vaccinia virus, polio virus, influenza virus, Japanese encephalitis virus, yellow fever virus, measles virus, rubella virus, mumps virus, hepatitis B virus, adeno virus, Epstein-Barr virus, distemper virus, rabies virus, Sendai virus and Newcastle disease virus.

3. The process as set forth in claim 1, wherein said water-soluble conjugate is formed by covalently linking said saccharide to said pathogenic virus via diazo-coupling, formation of a peptide bond, alkylation or cross-linking.

4. A process as set forth in claim 3, wherein said virus is a member selected from the group consisting of Japanese encephalitis virus, Sendai virus, and Newcastle disease virus.

5. A process as set forth in claim 1, wherein said virus is bound to said polysaccharide by peptide linkage.

6. A process as set forth in claim 1, wherein said virus is bound to said polysaccharide by diazo linkage.

7. A process as set forth in claim 1, wherein said activated polysaccharide bears a functional group selected from the group consisting of chloroacetyl, bromoacetyl, iodoacetyl, chlorotriazinyl groups, and p-aminobenzyl, p-aminobenzoyl, m-aminobenzyl, m-aminobenzoyl, m-aminoanisoyl, m-aminobenzyl oxymethyl, 3-(p-aminophenoxy)-2-hydroxypropionyl, 3-(amino-m-methylanilino)-5-chlorotriazinyl groups in the form of a diazonium salt.

8. A virus vaccine having a substantially diminished immunoglobulin E antibody producibility and substantially enhanced producibility of immunoglobulin G and immunoglobulin M antibodies prepared by the process claimed in claim 1.

* * * * *